United States Patent [19]

Remy

[11] 4,104,398

[45] Aug. 1, 1978

[54] 3-LOWER ALKOXYCYPROHEPTADINES AS SEROTONIN INHIBITORS

[75] Inventor: David C. Remy, North Wales, Pa.

[73] Assignee: Merck & Co., Inc., Rahway, N.J.

[21] Appl. No.: 713,773

[22] Filed: Aug. 12, 1976

[51] Int. Cl.$^2$ ................. C07D 211/70; A61K 31/445
[52] U.S. Cl. ................................ 424/267; 260/293.62
[58] Field of Search ..................... 260/293.62; 424/267

[56] References Cited

U.S. PATENT DOCUMENTS 3,014,911  12/1961  Engelhardt .......................... 260/293

OTHER PUBLICATIONS

Houben–Weyl, Methoden d. Org. Chem.: Sauerstoff-Verbindungen I, Teil 3, pp. 75–79.

*Primary Examiner*—Cecilia M. S. Jaisle
*Attorney, Agent, or Firm*—William H. Nicholson; Harry E. Westlake, Jr.

[57] ABSTRACT

The levorotatory enantiomers of 3-loweralkoxy-cyproheptadines are potent antiserotonin agents with a lower order of antihistaminic activity and substantially free of any anticholinergic activity. They are prepared by treatment of the levorotatory enantiomer of 3-iodocyproheptadine with an alkali metal lower alkoxide in the presence of copper powder.

6 Claims, No Drawings

3-LOWER ALKOXYCYPROHEPTADINES AS SEROTONIN INHIBITORS

BACKGROUND OF THE INVENTION

This invention is concerned with the levorotatory enantiomers of 3-lower alkoxycyproheptadines, potent antiserotonin agents with a low order of antihistaminic activity and substantially free of any anticholinergic activity. Antiserotonin agents are useful in the prophylactic treatment of vascular headache such as migraine and cluster headaches.

Lower alkoxycyproheptadines are disclosed and generically claimed in U.S. Pat. No. 3,014,911 and 3-methoxycyproheptadine is specifically disclosed therein. However, there is no suggestion that the lower alkoxy compounds disclosed are racemic mixtures; that stable dextroand levorotatory forms could be synthesized; nor that the enantiomers thereof would have different pharmacological activities.

The racemic 3-lower alkoxy derivatives are potent antiserotonin agents with a modest degree of antihistaminic activity, but like most such agents they cause annoying side effects such as dry mouth and blurring of the vision, resulting from concomittant anticholinergic properties.

It has now been found that 3-lower alkoxycyproheptadines do exist in stable enantiomeric forms and, surprisingly, that the levorotatory enantiomers are invested with all of the antiserotonin activity found in the racemates, whereas the anticholinergic activity of the racemates resides in the dextrorotatory enantiomers. This separation of pharmacological properties is extremely important from a therapeutic viewpoint in that the undesirable anticholinergic side effects are eliminated.

Thus, it is an object of this invention to provide the levorotatory enantiomers of 3-lower alkoxycyproheptadines and pharmaceutically acceptable salts thereof, a process for their syntheses, pharmaceutical formulations thereof, and a method of producing an antiserotonin effect in a patient in need of such treatment by administration of one of the novel compounds of this invention.

DETAILED DESCRIPTION OF THE INVENTION

The novel compounds of this invention are the levorotatory enantiomers of 3-lower alkoxycyproheptadine, otherwise designated as (—)-3-lower alkoxycyproheptadine, or (—)-1-methyl-4-(3-lower alkoxy-5H-dibenzo[a,d]cyclohepten-5-ylidene)piperidine. The term "lower alkoxy" is meant to include alkoxy groups of 1 to 4 carbon atoms.

A preferred embodiment of the novel compounds of this invention is (—)-3-methoxycyproheptadine or pharmaceutically acceptable salt thereof.

The salts contemplated to be within the scope of this invention are acid addition salts prepared from inorganic or organic acids known in the art to provide pharmaceutically accpetable salts, such as hydrochloric, phosphoric, hydrobromic, sulfuric, maleic, succinic, ethane disulfonic acid, or the like.

The novel process of this invention comprises heating a mixture of (—)-3-iodocyproheptadine, an excess of an alkali metal lower alkoxide, preferably a sodium lower alkoxide, and an excess of copper powder in an inert organic solvent until reaction is complete. The temperature at which the reaction is conducted may be from about 50° C. to about 150° C., but usually at or below the boiling point of the solvent, and preferably at about steam bath temperature, 100° C. The solvent can be any inert organic liquid capable of dissolving the alkoxide and iodocyproheptadine starting material, preferably dimethyl formamide. The reaction is completed in 1 to about 5 hours.

The novel method of treatment of this invention comprises administration of a (—)-3-lower alkoxycyproheptadine or pharmaceutically acceptable salt thereof, to a patient in need of antiserotonin therapy at a rate of from 0.014 to about 0.07 mg/kg/day, preferably at a rate of 0.04 to about 0.06 mg/kg/day. The novel compound may be administered orally, parenterally, or rectally.

The novel pharmaceutical compositions of this invention comprise an art-recognized pharmaceutical carrier and an effective amount of a (—)-3-lower alkoxycyproheptadine or pharmaceutically acceptable salt thereof. A unit dosage form comprises preferably from 0.5 mg. to about 1.0 mg. of active ingredient. For oral use the dosage forms may be in the form of tablets, capsules, syrups, suspensions or any art-recognized orally administrable form. For parenteral use, doses may be in the form of sterile solutions in aqueous, oily or emulsion mediums. For rectal administration, they may be in one of the usual suppository forms.

The following examples illustrate the chemical syntheses of the novel compounds of this invention and the preparation of the novel pharmaceutical formulations and are not meant to limit the invention to particular reagents and conditions employed therein.

EXAMPLE 1

(—)-1-Methyl-4-(3-methoxy-5H-dibenzo[a,d]cyclohepten-5-ylidene)piperidine

Step A: Preparation of 3-amino-5H-dibenzo[a,d]cyclohepten-5-one

3-Bromo-5H-dibenzo[a,d]cyclohepten-5-one (25 g., 0.088 mole), copper turnings (1.14 g., 0.018 mole), cuprous chloride (0.94 g., 0.009 mole), and concentrated aqueous ammonia (50 ml.) are agitated together at 195° in a steel bomb for 24 hours.

The cooled mixture is removed from the vessel, and the large solid mass broken up mechanically and dissolved in warm chloroform (ca 150 ml.). The aqueous residue from the reaction is extracted once with chloroform, and the combined chloroform fractions are washed with water, dried over sodium sulfate, filtered, and evaporated in vacuo to give 18.9 g. of crude yellow solid.

The crude product is ground in a mortar and recrystallized from ethanol (ca 200 ml.). The solid obtained is dissolved in warm chloroform, treated with about 8 g. of silica gel, filtered, and evaporated in vacuo to give 16 g. of 3-amino-5H-dibenzo[a,d]cyclohepten-5-one.

Step B: Preparation of 3-iodo-5H-dibenzo[a,d]cyclohepten-5-one

3-Amino-5H-dibenzo[a,d]cyclohepten-5-one (50 g., 0.226 mole) is slurried in 150 ml. of concentrated hydrochloric acid. Ice (150 ml.) is added, and the stirred mixture cooled in an ice bath and diazotized by dropwise addition of sodium nitrite solution (17 g., 0.248 mole in 80 ml. of water) over 45 minutes. The temperature is held below 5° throughout the addition. The mixture is stirred for an additional 15 minutes and poured slowly into a stirred solution of 160 g. (1 mole) of potassium iodide in 100 ml. of water. The mixture is stirred at room temperature for 1 hour, then stored overnight in the refrigerator.

The resulting slurry is filtered and the filtrate is extracted once with chloroform. The solids are extracted several times with hot chloroform, and the combined chloroform fractions washed with dilute sodium bisulfite and with water, and dried over sodium sulfate. Residual solid from the chloroform extraction is discarded.

The chloroform solution is combined with 100 g. of silica gel, evaporated in vacuo, then stirred with 1:1 chloroform/hexane and added to a column of 1 kg. of silica gel. The column is packed and eluted with 1:1 chloroform hexane. The product fraction, which is eluted after about 3.5 liters of fore-run, is evaporated in vacuo to give the 3-iodo-5H-dibenzo[a,d]cyclohepten-5-one (39.7 g., 53%) as a white solid, m.p. 97.5°–99°.

Step C: Preparation of (±)-1-methyl-4-(3-iodo-5H-dibenzo[a,d]cyclohepten-5-ylidene)piperidine To an ice-cooled solution of 10.00 g. (0.0301 mol) of 3-iodo-5H-dibenzo[a,d]cyclohepten-5-one in 100 ml. of dry tetrahydrofuran is added dropwise 64 ml. of 0.47M 1-methyl-4-piperidylmagnesium chloride in tetrahydrofuran. The solution is stirred one hour at room temperature, and then the tetrahydrofuran is removed on a rotary evaporator. The red-oily residue that remains is dissolved in benzene and water is added dropwise until a clear benzene supernatant and a gelatinous aquoeus phase is obtained. The benzene phase is decanted and the gelatinous aqueous phase is extracted with two 100 ml. portions of hot benzene. The combined benzene extracts are concentrated. The residue that remains is triturated with acetonitrile, and the crystalline product is collected by filtration, washed with cold acetonitrile and dried to give 5.95 gm. (46%) of 1-methyl-4-(3-iodo-5-hydroxy-5H-dibenzo[a,d]cyclohepten-5-yl)piperidine.

A solution of 3.23 g. of 1-methyl-4-(3-iodo-5-hydroxy-5H-dibenzo[a,d]cyclohepten-5-yl)piperidine, 30 ml. of trifluoroacetic acid and 10 ml. of trifluoroacetic anhydride is refluxed for 6 hours. The solution is concentrated on a rotary evaporator and the residue is made basic with 5% sodium hydroxide solution. The oil that precipitates is extracted into ether, and this ether phase is washed with water, dried over magnesium sulfate, filtered, and the ether removed on a rotary evaporator. The residue is triturated with acetonitrile, collected and dried to give 2.36 g. of material. This material is recrystallized from ether acetate to give pure (±)-1-methyl-4-(3-iodo-5H-dibenzo[a,d]cyclohepten-5-ylidene)-piperidine, m.p. 166°–170°.

Anal. Calcd. for $C_{21}H_{20}IN$: C, 61.03; H, 4.88; N, 3.38; I, 30.70. Found: C, 61.35; H, 5.01; N, 3.30; I, 30.62.

Step D: Preparation of (−)-1-methyl-4-(3-iodo-5H-dibenzo[a,d]cyclohepten-5-ylidene)piperidine To a solution of 4.60 g. (0.0111 mol) of (±)-1-methyl-4-(3-iodo-5H-dibenzo[a,d]cyclohepten-5-ylidene)-piperidine in 100 ml. of hot absolute ethanol is added 4.30 g. (0.0111 mol) of di-p-toluoyl-d-tartaric acid dissolved in 45 ml. of warm absolute ethanol. The solution is stirred and allowed to cool to room temperature. The crystalline precipitate that forms is removed by filtration, washed with cold absolute ethanol, and dried at 100° in vacuo to give 2.36 g. of material designated A. The clear ethanol filtrate and washings, which are combined and concentrated by boiling to 50 ml., are designated B.

The 2.36 g. of A is recrystallized from absolute ethanol four times to give a product that has a constant rotation, m.p. 156°–157°; $[\alpha]_{589}^{25} = -129°$, $[\alpha]_{578}^{25} = -136°$, $[\alpha]_{546}^{25} = -162°$, $[\alpha]_{436}^{25} = -371°$ (c = 0.00407 g./ml. pyridine). This material, 0.35 g. is suspended in a small amount of water and is treated with sodium hydroxide solution. The free base that precipitates is extracted into ether, washed with water, and dried over magnesium sulfate. After filtering, the ether is removed on a rotary evaporator. The white solid that remains is recrystallized from acetonitrile to give 0.12 g. of (−)-1-methyl-4-(3-iodo-5H-dibenzo[a,d]cyclohepten-5-ylidene)piperidine, m.p. 184°–190°; $[\alpha]_{589}^{25} = -141°$, $[\alpha]_{578}^{25} = -149°$, $[\alpha]_{546}^{25} = -180°$, $[\alpha]_{436}^{25} = -437°$ (c = 0.00356 g./10 m. $CHCl_3$).

Anal. Calcd. for $C_{21}H_{20}IN$: C, 61.03; H, 4.88; N, 3.38; I, 30.70. Found: C, 60.66; H, 5.25; N, 3.28; I, 30.83.

DEXTROROTATORY ISOMER

The ethanol filtrate and washings, designated B, are concentrated on a rotary evaporator. The residue is treated with sodium carbonate solution. The free base that precipitates is extracted into ether. Evaporation of the ether gives 2.23 g. of a solid that is dissolved in 75 ml. of hot absolute ethanol and treated with 2.18 g. of di-p-toluoyl-1-tartaric acid monohydrate in 20 ml. of hot absolute ethanol. The solution is stirred and concentrated by boiling to 45 ml. The crystalline precipitate that forms on cooling is removed by filtration, washed with cold absolute ethanol, and dried at 100° in vacuo to give 2.00 g. of material. This material is recrystallized from absolute ethanol to give a product that has a constant rotation, m.p. 155°–157°; $[\alpha]_{589}^{25} = +128°$, $[\alpha]_{578}^{25} = +136°$, $[\alpha]_{546}^{25} +162°$, $[\alpha]_{436}^{25} = +372°$, (c = 0.00181 g./ml pyridine). This material, 0.53 g., is suspended in a small amount of water and is treated with sodium hydroxide solution. The free base that precipitates is extracted into ether, washed with water, and dried over magnesium sulfate. After filtering, the ether is removed on a rotary evaporator. The residue is triturated with acetonitrile, collected by filtration, and dried to give 0.18 g. of (+)-1-methyl-4-(3-iodo-5H-dibenzo[a,d]cyclohepten-5-ylidene)piperidine, m.p. 188°–191°; $[\alpha]_{589}^{25} = +139°$, $[\alpha]_{578}^{25} = +145°$, $[\alpha]_{546}^{25} = +175°$, $[\alpha]_{436}^{25} = +430°$, (c = 0.00137 g./ml. $CHCl_3$).

Anal. Calcd. for $C_{21}H_{20}IN$: C, 61.03; H, 4.88; N, 3.38. Found: C, 61.27; H, 5.21; N, 3.20.

Step E: Preparation of (−)-1-methyl-4-(3-methoxy-5H-dibenzo[a,d]cyclohepten-5-ylidene)piperidine A mixture of 3.74 g. (0.00905 mol) of (−)-1-methyl-4-(3-iodo-5H-dibenzo[a,d]cyclohepten-5-ylidene)piperidine, $[\alpha]_{589} -142°$, 9.77 g. (0.181 mol) of sodium methoxide, 5.56 g. of electrolytic copper dust, and 87 ml. of DMF is stirred and heated on a steam bath for 2.5 hours. After cooling, 150 ml. of water and 150 ml. of ether is added to the mixture, and, after stirring, the mixture is filtered through a pad of celite. The ether phase is separated, washed with water, dried over magnesium sulfate, filtered, and the ether is removed on a rotary evaporator. The residue, 2.67 g., is dissolved in 50 ml. of warm acetonitrile. On standing, the solution deposits crystals. The supernatant, containing the desired product, is decanted from the crystals. Evaporation of the solvent gives 2.0 g. of solid which is recrystallized from 40 ml. of hexane. The product then is recrystallized from 8 ml. of acetonitrile. The product is collected, washed with ice cold acetonitrile, and dried to give 1.0 g. of (—)-1-methyl-4-(3-methoxy-5H-dibenzo[a,d]cyclohepten-5-ylidene)piperidine, m.p. 115°–116°; $[\alpha]_{589}$ —153°, $[\alpha]_{578}$ —163, $[\alpha]_{546}$ —198°, $[\alpha]_{436}$ —515° (c, 0.491, CHCl$_3$).

Anal. Calcd. for $C_{22}H_{23}NO$: C, 83.24; H, 7.30; N, 4.41. Found: C, 83.55; H, 7.44; N, 4.59.

Employing the procedure substantially as described in Example 1, Step E, but substituting for the sodium methoxide used therein, an equimolecular amount of sodium ethoxide, sodium n-propoxide, sodium isopropoxide, sodium n-butoxide, sodium sec.-butoxide, or sodium t-butoxide, there is produced respectively (—)-3-ethoxycyproheptadine, (—)-3-n-propoxycyproheptadine, (—)-3-isopropoxycyproheptadine, (—)-3-n-butoxycyproheptadine, (—)-3-sec.-butoxycyproheptadine, or (—)-3-t-butoxycyproheptadine.

EXAMPLE 2

(+)-1-Methyl-4-(3-methoxy-5H-dibenzo[a,d]cyclohepten-5-ylidene) piperidine

A mixture of 1.40 g. (0.00339 mol) of (+)-1-methyl-4-(3-iodo-5H-dibenzo[a,d]cyclohepten-5-ylidene, $[\alpha]_{589}$ +142°, 3.66 g. (0.0678 mole) of sodium methoxide, 4.31 g. (0.0678 mol) of electrolytic copper dust, and 33 ml. of DMF is stirred and heated on a steam bath for one hour. After cooling, the mixture is poured into water, and the precipitate that forms is extracted into ether. The mixture is filtered through a pad of Celite. The ether phase is separated, washed with water, dried over magnesium sulfate, filtered, and the ether is removed on a rotary evaporator. The oily residue is triturated with ice cold acetonitrile, and the solid that forms is removed by filtration. This solid is recrystallized from 5 ml. of acetonitrile. On standing, the solution deposits crystals. The supernatant, containing the desired product, is decanted from these crystals. On further standing, this supernatant liquid deposits crystals. These crystals are collected by filtration, washed with a small amount of ice cold acetonitrile, and dried to give (+)-1-methyl-4-(3-methoxy-5H-dibenzo[a,d]cyclohepten-5-ylidene)piperidine, $[\alpha]_{589}$ +147°. Recrystallization from acetonitrile gives analytically pure product, m.p. 112.5°–114.5°; $[\alpha]_{589}$ +147°, $[\alpha]_{578}$ +157°, $[\alpha]_{546}$ +191°, $[\alpha]_{436}$ +497° (C, 0.150, CHCl$_3$).

Anal. Calcd. for $C_{22}H_{23}NO$: C, 83.24; H, 7.30; N, 4.41. Found: C, 82.75: H, 7.47; N, 4.59.

EXAMPLE 3

Preparation of Tablet Formulation

| Ingredient | Milligrams per Tablet |
| --- | --- |
| (-)-3-methoxycyproheptadine | 1.00 |
| Lactose | 200 |
| Corn Starch (for mix) | 50 |
| Corn Starch (for paste) | 50 |
| Magnesium stearate | 6 |

The active ingredient, lactose, and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine.

What is claimed is:

1. A compound, (—)-1-methyl-4-(3-lower alkoxy-5H-dibenzo[a,d]cyclohepten-5-ylidene)piperidine, or pharmaceutically acceptable salt thereof.

2. The compound of claim 1, which is (—)-1-methyl-4-(3-methoxy-5H-dibenzo[a,d]cyclohepten-5-ylidene)-piperidine or a pharmaceutically accpetable salt thereof.

3. A pharmaceutical antiserotonin composition in unit dosage form comprising a pharmaceutical carrier and an effective amount of (—)-1-methyl-4-(3-lower alkoxy-5H-dibenzo[a,d]-cyclohepten-5-ylidene)piperidine.

4. The pharmaceutical antiserotonin composition of claim 3 comprising a pharmaceutical carrier and an effective amount of (—)-1-methyl-4-(3-methoxy-5H-dibenzo [a,d]cyclohepten-5-ylidene)piperidine.

5. A method of inhibiting serotonin which comprises the administration to a patient in need of such treatment of an effective amount of (—)-1-methyl-4-(3-lower alkoxy-5H-dibenzo[a,d]cyclohepten-5-ylidene)piperidine.

6. The method of claim 5 which comprises the administration to a patient in need of such treatment of an effective amount of (—)-1-methyl-4-(3-methoxy-5H-dibenzo[a,d]cyclohepten-5-ylidene)piperidine.

* * * * *